United States Patent [19]

Kirst

[11] 4,436,733
[45] Mar. 13, 1984

[54] 4''- AND 3-ESTER DERIVATIVES OF DMT AND DMOT

[75] Inventor: Herbert A. Kirst, Indianapolis, Ind.

[73] Assignee: Eli Lilly and Company, Indianapolis, Ind.

[21] Appl. No.: 354,262

[22] Filed: Mar. 3, 1982

[51] Int. Cl.³ .................... A61K 31/71; C07H 17/08
[52] U.S. Cl. .................................... 424/180; 536/7.1
[58] Field of Search ........................ 424/180; 536/7.1

[56] References Cited

U.S. PATENT DOCUMENTS

| | | | |
|---|---|---|---|
| 4,056,616 | 11/1977 | Reimann et al. | 424/180 |
| 4,092,473 | 5/1978 | Okamoto et al. | 536/17 |
| 4,161,523 | 7/1979 | Weinstein et al. | 424/181 |
| 4,201,843 | 5/1980 | Okamoto et al. | 435/76 |
| 4,205,163 | 5/1980 | Mori et al. | 536/17 |
| 4,242,504 | 12/1980 | Sakakibara et al. | 536/17 R |
| 4,268,665 | 5/1981 | Sakakibara et al. | 536/17 R |
| 4,321,361 | 3/1982 | Baltz et al. | 536/17 R |
| 4,321,362 | 3/1982 | Baltz et al. | 536/17 R |

FOREIGN PATENT DOCUMENTS 2058765 4/1981 United Kingdom .

OTHER PUBLICATIONS

A. A. Nagel et al., *J. Org. Chem.* 44, 2050–2052, (1979).
R. Okamoto et al., *J. Antibiotics* 32, 542–544, (1979).
R. Okamoto et al., *J. Antibiotics* 33, 1300–1308, (1980).
R. Okamoto et al., *J. Antibiotics* 33, 1309–1315, (1980).
M. Tsuchiya et al., *J. Antibiotics* 34, 305–312, (1981).
T. Fujiwara and H. Yanagibara, (Toyo Jozo Co.), Table 1 from Paper on 19-Deformylated desmycosin/tylosin, Presented at 1980 Conference of Japan Pharmaceutical Association.
Derwent Abstract No. 66634C of Japanese Unexamined Patent 5043-013, (Sanraku Ocean), Mar. 26, 1980.
Derwent Abstract No. 79659C of Japanese Unexamined Patent 5122-798, (Toyo Jozo), Sep. 20, 1980.
Derwent Abstract No. 74422C of Japanese Unexamined Patent 5115-899, (Toyo Jozo), Sep. 6, 1980.
H. Sakakibara et al., *J. Antibiotics* 34 (8), 1001–1010, (1981).
Y. Shimauchi et al., *J. Antibiotics* 34 (2), 245–248, (1981).
Y. Shimauchi et al., *Antibiotics* 34 (3), 284–292, (1980).
T. Nakamura et al., *Chem. Letters 1978*, 1293–1296.
R. Okamoto et al., *J. Ferment. Technol.* 57 (6), 519–528, (1979).
Derwent Abstract 17436C of Japanese Unexamined Patent 5011-557, Jan. 26, 1980.
Derwent Abstract 17437C of Japanese Unexamined Patent 5011-558, Jan. 26, 1980.
Derwent Abstract 27592A of Japanese Unexamined Patent 3021-182, Feb. 27, 1978, Equivalent to Japanese Examined Patent J80023273, Jun. 21, 1980.
Derwent Abstract 35433D of Japanese Unexamined Patent 6032-494, Apr. 1, 1981.
Derwent Abstract 03335B of Japanese Unexamined Patent 3137-982, Dec. 1, 1978.

*Primary Examiner*—Johnnie R. Brown
*Attorney, Agent, or Firm*—Nancy J. Harrison; Arthur R. Whale

[57] ABSTRACT

4''- and 3-Ester derivatives of 23-demycinosyltylosin (DMT) and 23-de(mycinosyloxy)tylosin (DMOT) of the formula:

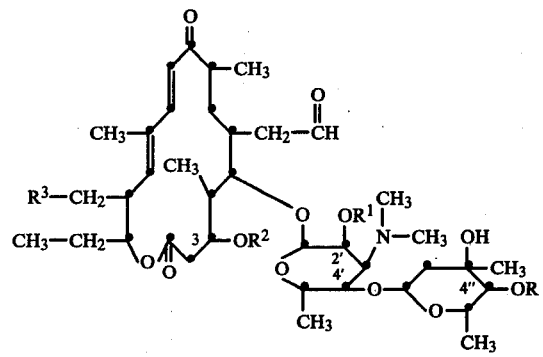

wherein R is hydrogen, optionally substituted $C_1$-$C_5$-alkanoyl or optionally substituted benzoyl, phenylacetyl or phenoxyacetyl; $R^1$ is hydrogen, optionally substituted $C_1$-$C_5$-alkanoyl or optionally substituted benzoyl, phenylacetyl, or phenylpropionyl; $R^2$ is hydrogen, optionally substituted $C_1$-$C_5$-alkanoyl, or optionally substituted benzoyl, phenylacetyl, phenylpropionyl, phenoxyacetyl or phenylthioacetyl; $R^3$ is hydrogen or $R^4O$—; and $R^4$ is hydrogen or a specified acyl group provided that one of R or $R^2$ must be other than hydrogen and that, when $R^1$ is hydrogen, $R^3$ is hydrogen or —OH and $R^2$ is acetyl, R cannot be hydrogen, acetyl, n-butyryl or isovaleryl and, when R and $R^1$ are hydrogen and $R^3$ is hydrogen or —OH, $R^2$ cannot be propionyl; and salts thereof are useful antibiotics or intermediates to antibiotics.

53 Claims, No Drawings

4''- AND 3-ESTER DERIVATIVES OF DMT AND DMOT

SUMMARY OF THE INVENTION

This invention relates to 4''- and 3-ester derivatives of 23-demycinosyltylosin (DMT) and 23-de(mycinosyloxy)tylosin (DMOT) having formula 1:

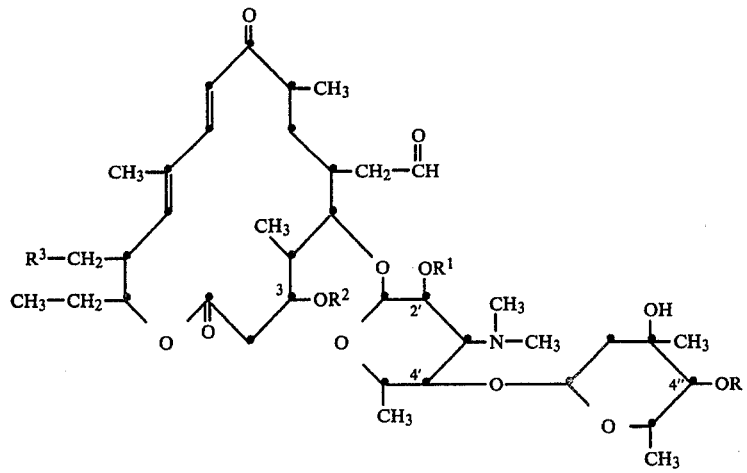

wherein R is hydrogen, optionally substituted $C_1$–$C_5$-alkanoyl or optionally substituted benzoyl, phenylacetyl or phenoxyacetyl; $R^1$ is hydrogen, optionally substituted $C_1$–$C_5$-alkanoyl or optionally substituted benzoyl, phenylacetyl, or phenylpropionyl; $R^2$ is hydrogen, optionally substituted $C_1$–$C_5$-alkanoyl, or optionally substituted benzoyl, phenylacetyl, phenylpropionyl, phenoxyacetyl or phenylthioacetyl; $R^3$ is hydrogen or $R^4O$—; and $R^4$ is hydrogen or a specified acyl group, provided that one of R or $R^2$ must be other than hydrogen and that, when $R^1$ is hydrogen, $R^3$ is hydrogen or —OH and $R^2$ is acetyl, R cannot be hydrogen, acetyl, n-butyryl or isovaleryl and, when R and $R^1$ are hydrogen and $R^3$ is hydrogen or —OH, $R^2$ cannot be propionyl, and to the acid addition salts of these compounds. The compounds of this invention are useful as antibiotics and/or as intermediates to antibiotics. This invention also relates to pharmaceutical compositions comprising these compounds and to methods of treatment wherein these compounds or compositions are administered to obtain an antibiotic effect or to enhance growth promotion in animals.

DETAILED DESCRIPTION OF THE INVENTION

This invention relates to new antibiotics. In particular, this invention relates to 4''- and 3-ester derivatives of DMT and DMOT and to their acid addition salts. This invention also relates to methods of treating certain infections with, methods of promoting growth in animals with, and pharmaceutical compositions comprising the specified ester derivatives of DMT and DMOT and their pharmaceutically acceptable acid addition salts.

New, improved antibiotics are continually in demand. In addition to antibiotics which are useful for treating human diseases, improved antibiotics are also needed in the veterinary field. Increased potency, expanded spectrum of bacterial inhibition, increased in vivo efficacy, and improved pharmaceutical properties (such as greater oral absorption, higher blood or tissue concentrations, longer body half life, and more advantageous rate or route of excretion and rate or pattern of metabolism) are some of the goals for improved antibiotics.

DMT is an antibiotic described by Richard H. Baltz, Gene M. Wild, and Eugene T. Seno in their copending application entitled DEMYCINOSYLTYLOSIN AND PROCESS FOR ITS PRODUCTION, Ser. No. 156,854, filed June 12, 1980, now U.S. Pat. No. 4,321,361.

DMOT is another antibiotic described by Richard H. Baltz, Gene H. Wild and Eugene T. Seno in a copending application entitled DE(MYCINOSYLOXY)TYLOSIN AND PROCESS FOR ITS PRODUCTION, Ser. No. 156,855, filed June 12, 1980, now U.S. Pat. No. 4,321,362. The structurs of DMT and DMOT are shown in formulas 2 and 3, respectively:

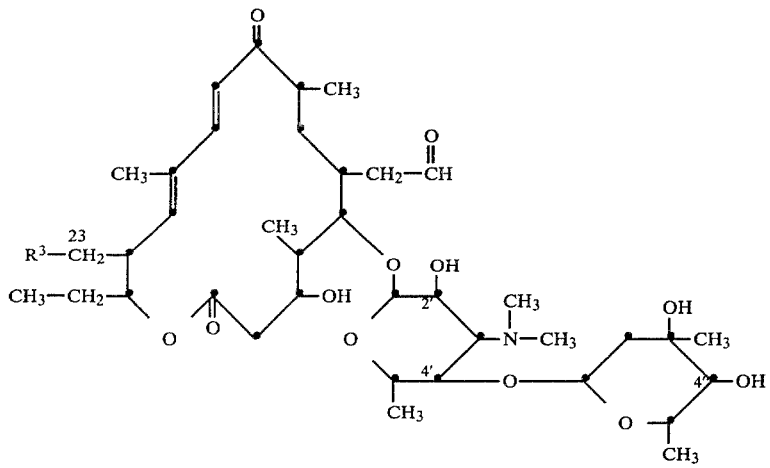

DMT (2): $R^3 = OH$
DMOT (3): $R^3 = H$

The 4″-ester derivatives of DMT and DMOT of this invention are compounds of formula 1 wherein:

R is hydrogen, optionally substituted $C_1$-$C_5$-alkanoyl or optionally substituted benzoyl, phenylacetyl or phenoxyacetyl;

$R^1$ is hydrogen, optionally substituted $C_1$-$C_5$-alkanoyl or optionally substituted benzoyl, phenylacetyl, or phenylpropionyl;

$R^2$ is hydrogen, optionally substituted $C_1$-$C_5$-alkanoyl, or optionally substituted benzoyl, phenylacetyl, phenylpropionyl, phenoxyacetyl or phenylthioacetyl;

$R^3$ is hydrogen or $R^4O$—; and $R^4$ is hydrogen or an acyl group selected from:

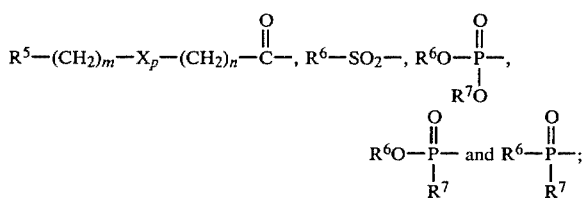

p is 0 or 1; m and n are integers from 0 to 4;

$R^5$ is hydrogen, halo, $C_1$-$C_4$-alkyl, $C_3$-$C_8$-cycloalkyl, phenyl, $C_5$-$C_8$-cycloalkenyl, naphthyl, indenyl, tetralinyl, decalinyl, adamantyl, 1-ethyl-1,4-dihydro-4-oxo[1,3]dioxolo[4,5-g]cinnolin-3-yl(cinnoxacinyl), a monocyclic heterocyclic ring system comprising 3 to 8 atoms or a bicyclic heterocyclic ring system comprising 6 to 11 atoms, provided that at least 1 atom of the ring system is carbon and at least 1 atom of the ring system is a heteroatom selected from O, N, and S; and wherein $R^5$ and the connecting alkyl groups —$(CH_2)_m$— and —$(CH_2)_n$— are optionally substituted by one or two halo, methyl, ethyl, methoxy, amino, N-protected-amino, methylamino, dimethylamino, nitro, acetoxy, acetamido, azido, carbomethoxy, carboxamido, cyano, or hydroxyl groups, provided that, if the substituent is other than halo or alkyl, there can be no more than one substituent on any connecting —$CH_2$— group;

X is O, S, —NH—, —N($CH_3$)—, —C≡C—, —CH=CH—, —C($CH_3$)=CH—, —CH=C($CH_3$)— or —C($CH_3$)=C($CH_3$)—;

$R^6$ and $R^7$ are $C_1$-$C_5$-alkyl or optionally substituted phenyl or benzyl;

and further provided that one of R or $R^2$ must be other than hydrogen and that, when $R^1$ is hydrogen, $R^3$ is hydrogen or —OH and $R^2$ is acetyl, R cannot be hydrogen, acetyl, n-butyryl or isovaleryl and, when R and $R^1$ are hydrogen and $R^3$ is hydrogen or OH, $R^2$ cannot be propionyl. The acid addition salts of these compounds are also part of this invention.

The term "optionally substituted $C_1$-$C_5$-alkanoyl" as used herein means an acyl moiety derived from a carboxylic acid containing from one to five carbon atoms. In such a moiety, the alkyl group can be straight, branched, or cyclic and can optionally bear one to three halo substituents. Halo substituents are selected from the group consisting of Cl, Br and F. Acetyl, chloroacetyl, trichloroacetyl, trifluoroacetyl, propionyl, n-butyryl, isobutyryl, n-valeryl, and isovaleryl are examples of such groups.

The terms "optionally substituted benzoyl, phenylacetyl or phenoxyacetyl", "optionally substituted benzoyl, phenylacetyl or phenylpropionyl", "optionally substituted phenyl or benzyl" and "optionally substituted benzoyl, phenylacetyl, phenylpropionyl, phenoxyacetyl or phenylthioacetyl" mean that in each of these moieties the phenyl portion is optionally substituted by from one to five halo or methyl or by from one to two methoxyl, nitro or hydroxyl groups.

The terms "$C_1$-$C_4$-alkyl" and "$C_1$-$C_5$-alkyl" as used herein mean a straight- or branched-chain alkyl group containing from one to four or from one to five carbon atoms, respectively. Such groups include methyl, ethyl, n-propyl, isopropyl, n-butyl, sec-butyl, isobutyl and tert-butyl and, for the latter, n-pentyl and isopentyl, and the like.

The term "$C_3$-$C_8$-cycloalkyl" means a saturated ring having from three to eight carbon atoms in the ring. Examples of such rings are cyclopropyl, cyclobutyl, cyclopentyl, cyclohexyl, and cyclooctyl. By "$C_5$-$C_8$-cycloalkenyl" is meant a carbocylic ring which contains from five to eight carbon atoms and which also contains one or two double bonds. Cyclohexadienyl, cyclohexenyl, cyclopentenyl, and cyclooctadienyl are examples of such rings.

The term "monocyclic or bicyclic heterocyclic ring system" as used herein includes saturated or unsaturated heterocyclic moieties containing at least one carbon atom and at least one heteroatom selected from oxygen, nitrogen and sulfur. Heterocyclic groups contemplated include:

unsaturated 3 to 8-membered monocyclic groups, for example, pyrrolyl, $\Delta^3$-pyrrolinyl, imidazolyl, pyrazolyl, pyridyl, pyrimidyl, pyrazinyl, pyridazinyl, triazinyl, triazolyl (e.g., 4H-1,2,4-triazolyl, 1H-1,2,3-triazolyl, etc.), tetrazolyl (e.g., 1H-tetrazolyl, 2-tetrazolyl, etc.), oxazolyl, isoxazolyl, oxadiazolyl (e.g., 1,2,4-oxadiazolyl, 1,3,4-oxadiazolyl, 1,2,5-oxadiazolyl, etc.), thiazolyl, isothiazolyl, thiadiazolyl (e.g., 1,2,4-thiadiazolyl, 1,3,4-thiadiazolyl, 1,2,5-thiadiazolyl, etc.), thienyl, furanyl, etc;

saturated 3 to 8-membered monocyclic groups, for example, pyrrolidinyl, imidazolidinyl, piperidinyl, piperazinyl, morpholinyl, thiazolidinyl, tetrahydrofuranyl, tetrahydrothienyl, tetrahydropyranyl, dioxanyl, etc.;

unsaturated 6 to 11-membered bicyclic groups, for example, indolyl, isoindolyl, coumaronyl, benzothiofuranyl, benzimidazolyl, quinolyl, isoquinolyl, benzopyrazolyl, cinnolinyl, quinazolinyl, benzoxazolyl, benzothiazolyl, benzoxazinyl, coumarinyl, etc.; and the like.

"N-protected-amino" means that the amino group is substituted by a suitable protecting group. Such a group must be one which is compatible with the other functional groups in DMT and which can be readily removed from the 23-O-acylated derivative. Examples of suitable protecting groups can be found in "Protective Groups in Organic Synthesis" by Theodora W. Greene, John Wiley & Sons, New York, 1981, Chapter 7.

When $R^4$ is an acyl group wherein X is —CH=CH—, —C(CH$_3$)$_2$=CH—, —CH=C(CH$_3$)— or —C(CH$_3$)=C(CH$_3$)—, the substituents on the double bond can be in either the cis or trans configuration.

Illustrative $R^4$ groups include those wherein:
(1) $R^4$ is

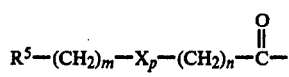

and
(a) $R^5$ is hydrogen or $C_1$-$C_4$-alkyl;
(b) p is 0;
(c) $R^5$ is optionally substituted phenyl;
(d) X is oxygen or —NH— and n is 0; or
(e) X is oxygen or sulfur and n is 1; and
(2) $R^4$ is $R^6$—SO$_2$ and
(a) $R^6$ is $C_1$-$C_5$-alkyl; or
(b) $R^6$ is optionally substituted phenyl.

The 4"- and 3-ester derivatives of this invention are prepared from DMT or DMOT via 2',23-diesters (DMT) or 2'-esters (DMOT). The preparation of DMT and its 2'-ester derivatives is described by Baltz et al. in application Ser. No. 156,854, which is incorporated herein by reference. The preparation of DMOT and its 2'-ester derivatives is described by Baltz et al. in application Ser. No. 156,855, which is incorporated herein by reference. 2',23-Diester derivatives of DMT and their preparation are described in my copending application entitled 23-ESTER DERIVATIVES OF DMT, Ser. No. 330,294, filed Dec. 14, 1981, now U.S. Pat. No. 4,396,613, which is also incorporated herein by reference.

The compounds of this invention can be prepared by esterifying a suitable 2',23-diester of DMT on the 4" and/or 3-hydroxyl groups or by esterifying a suitable 2'-ester of DMOT on the 4" and/or 3-hydroxyl groups by treatment with acylating agents using conventional methods. The 4"- or 3-monoesters and the 3,4"-diesters of DMOT and the 4",23-diesters; 3,23-diesters; and 4",3,23-triesters of DMT are then prepared by selectively removing the 2'-O-acyl substituent. 4"- or 3-Monoesters and 4",3-diesters of DMT can be prepared by removing the 23-O-acyl substituent when that substituent is a more readily removable group such as the trichloroacetyl group.

In the absence of external base, esterification of the 2'-hydroxyl group of DMT and DMOT is more facile than esterification of the remaining hydroxyl groups. Typical acylating agents include anhydrides, acyl halides (usually in combination with an acid scavenger), and active esters of organic acids. Acylation can also be achieved by using a mixture of an organic acid and a dehydrating agent such as N,N'-dicyclohexylcarbodiimide. Acylation can be monitored using standard techniques such as thin-layer chromatography (TLC) until the reaction is complete. Once formed, the desired 2'-ester derivatives can be separated and purified by known techniques.

In the case of DMT, the 23-hydroxyl group must be acylated next. If the 23-O-acyl group is to remain, it can be chosen from one of the groups specified. If the 23-O-acyl group is to be removed, it should be chosen from those groups which are more readily removed, such as the trichloroacetyl group.

The 4"-hydroxyl group of DMT or DMOT is only slightly more reactive than the 3-hydroxyl group. Acylation of a 2'-O-acyl-DMOT derivative or a 2',23-di-O-acyl-DMT derivative, therefore, usually leads to mixtures of 4"-O-acyl and 3,4"-di-O-acyl derivatives, but sometimes also leads to minor amounts of the 3-O-acyl derivative. Such mixtures can then be separated by standard procedures such as chromatography. When preparing 3-O-monoacyl compounds, it is preferable to acylate the 4"-hydroxyl group with a protecting group such as the trichloroacetyl group, then acylate the 3-hydroxyl group of this intermediate with the desired group, and subsequently remove the 4"-O-acyl-protecting group along with the 2'-O-acyl and, if required, 23-O-acyl protecting groups.

As discussed herein, certain ester derivatives of formula 1 are prepared via intermediates which have one or more hydroxyl groups protected by hydrolyzable O-acyl-protecting groups. Such groups may be located on the 2'- or 4"-hydroxyl group of DMT or DMOT and on the 23-hydroxyl group of DMT. The trichloroacetyl group is a particularly useful 23 and 4"-O-acyl-protecting group, and the acetyl group is a useful 2'-O-acyl-protecting group. Selective de-esterification can be accomplished using known procedures, such as warming or refluxing the protected intermediate in aqueous methanol. The de-esterification reaction can be monitored using standard techniques, such as TLC, to determine the time required for removal of the protecting group.

Reaction Schemes I and II, which follow, summarize the preparation of the ester derivatives of this invention. Scheme I describes the preparation of the DMOT derivatives, and Scheme II describes the preparation of the DMT derivatives. In each Scheme, "A" represents an acylation procedure; "B" represents a deacylation (deblocking) procedure; R, $R^1$, $R^2$ and $R^4$ are as herein defined except that none can be hydrogen; and $R^r$ represents a readily removable acyl group such as the trichloroacetyl group.

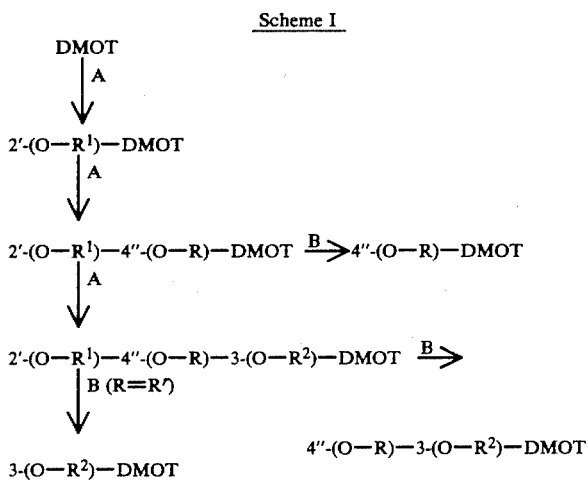

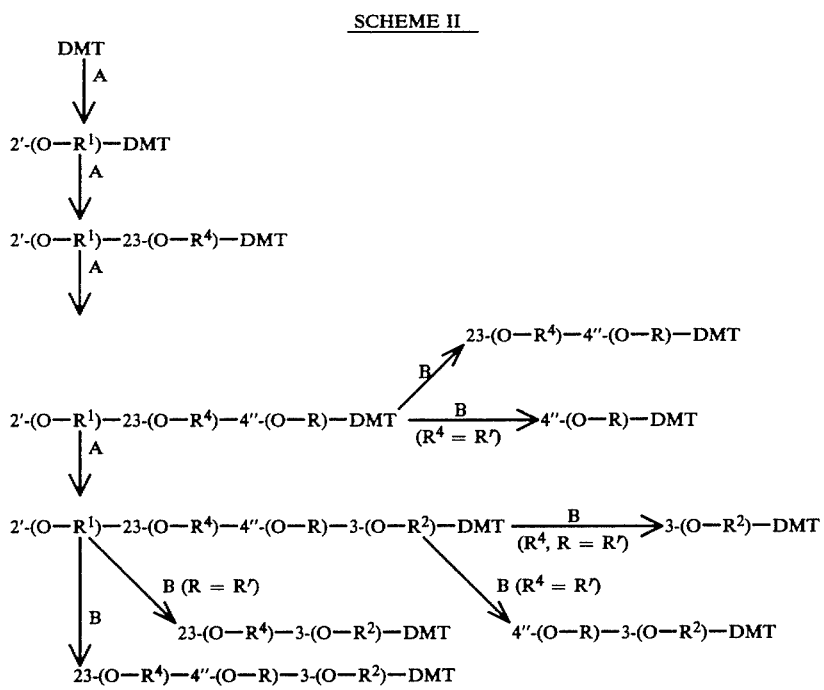

benzenesulfonic, sorbic, picric, benzoic, cinnamic, and like acids.

Pharmaceutically acceptable acid addition salts are an especially preferred group of salts of this invention.

DMT can be prepared by fermentation of *Streptomyces fradiae* NRRL 12170 under submerged aerobic conditions until a substantial level of antibiotic activity is produced. DMOT can be prepared by fermentation of another *S. fradiae* strain, NRRL 12171, in the same manner. DMT or DMOT can be extracted from the basified broth filtrate in which it is present with organic solvents such as ethyl acetate and can be further purified by extraction, chromatography, and/or crystallization. The DMT- and DMOT-producing strains of *Streptomyces fradiae* have been deposited and made part of the stock culture collection of the Northern Regional Research Center, Agricultural Research, North Central Region, 1815 North University Street, Peoria, Ill., 61604, from which they are available to the public under the accession numbers NRRL 12170 and NRRL 12171, respectively.

Illustrative esters of DMT of this invention, i.e. those compounds of formula 1 wherein $R^3 = R^4O-$, are listed in Table I.

TABLE I

Illustrative 4"- and 3-Ester Derivatives of DMT

The ester derivatives of this invention form acid addition salts. These acid addition salts are also useful as antibiotics and are a part of this invention. In another aspect, such salts are useful as intermediates, for example, for separating and purifying the ester derivatives. In addition, the salts have an improved solubility in water.

Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicylic, methanesulfonic,

| Compound No. | R (4") | $R^1$ (2') | $R^2$ (3) | $R^4$ (23) |
|---|---|---|---|---|
| 1 | acetyl | acetyl | H | acetyl |
| 2 | acetyl | H | H | acetyl |
| 3 | propionyl | acetyl | H | propionyl |
| 4 | propionyl | H | H | propionyl |
| 5 | phenylacetyl | acetyl | H | phenylacetyl |
| 6 | phenylacetyl | H | H | phenylacetyl |
| 7 | phenoxyacetyl | acetyl | H | phenoxyacetyl |
| 8 | H | acetyl | phenoxyacetyl | phenoxyacetyl |
| 9 | propionyl | acetyl | propionyl | propionyl |
| 10 | propionyl | H | propionyl | propionyl |
| 11 | trichloroacetyl | acetyl | H | trichloroacetyl |
| 12 | H | acetyl | trichloroacetyl | trichloroacetyl |

TABLE I-continued

Illustrative 4"- and 3-Ester Derivatives of DMT

| Compound No. | R (4") | R¹ (2') | R² (3) | R⁴ (23) |
|---|---|---|---|---|
| 13 | trichloroacetyl | acetyl | trichloroacetyl | trichloroacetyl |
| 14 | propionyl | acetyl | H | trichloroacetyl |
| 15 | propionyl | acetyl | propionyl | trichloroacetyl |
| 16 | propionyl | H | H | H |
| 17 | propionyl | H | propionyl | H |

Illustrative DMOT esters of this invention, i.e., those compounds of formula 1 wherein $R^3$=H, are listed in Table II.

TABLE II

Illustrative 4"- and 3-Esters of DMOT

| Compound No. | R (4") | R¹ (2') | R² (3) |
|---|---|---|---|
| 18 | isovaleryl | acetyl | H |
| 19 | isovaleryl | H | H |
| 20 | phenylacetyl | acetyl | H |
| 21 | phenylacetyl | H | H |
| 22 | propionyl | acetyl | H |
| 23 | propionyl | acetyl | propionyl |
| 24 | propionyl | H | H |
| 25 | propionyl | H | propionyl |

The 4"- and 3-ester derivatives of this invention inhibit the growth of pathogenic bacteria, especially gram-positive bacteria and Mycoplasma species. For example, Tables III and IV show the minimal inhibitory concentrations (MIC's) at which illustrative compounds inhibit certain bacteria. The MIC's in Table III were determined by standard agar-dilution assays. The MIC's in Table IV were obtained using a conventional broth-dilution microtiter test.

TABLE III

Antibiotic Activity of 4"- and 3-Ester Derivatives

| Test Organism | Test Compound[a] | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| *Staphylococcus aureus* X1.1 | 1 | 0.5 | 0.5 | 0.5 | 1 | 1 | 32 | 0.5 | 1 | 0.5 | 4 | 1 | 8 |
| *Staphylococcus aureus* V41[b] | 0.5 | 0.25 | 1 | 1 | 1 | 1 | 64 | 1 | 1 | 1 | 8 | 2 | 16 |
| *Staphylococcus aureus* X400[c] | 2 | 1 | 1 | 1 | 2 | 1 | 64 | 1 | 1 | 1 | 8 | 2 | 16 |
| *Staphylococcus aureus* S13E | 1 | 0.5 | 0.5 | 0.5 | 1 | 1 | 32 | 0.5 | 1 | 0.5 | 4 | 1 | 8 |
| *Staphylococcus epidermidis* EPI1 | 1 | 1 | 0.5 | 0.5 | 1 | 1 | 32 | 1 | 1 | 1 | 2 | 1 | 8 |
| *Staphylococcus epidermidis* EPI2 | 2 | 1 | 1 | 1 | 2 | 1 | 128 | 1 | 2 | 2 | 4 | 2 | 16 |
| *Streptococcus pyogenes* C203 | 0.5 | 0.25 | 0.25 | 0.25 | NT | 0.25 | 8 | 0.125 | 0.5 | 0.25 | 2 | 0.5 | 8 |
| *Streptococcus pneumoniae* Park I | 0.125 | 0.125 | 0.125 | 0.06 | NT | 0.125 | 1 | 0.125 | 0.25 | 0.125 | 0.25 | 0.125 | 2 |
| Streptococcus Group D X66 | 1 | 0.5 | 1 | 1 | 2 | 0.5 | 32 | 0.5 | 1 | 1 | 4 | 2 | 16 |
| Streptococcus Group 9960 | 1 | 0.5 | 1 | 0.5 | 2 | 0.5 | 16 | 0.25 | 1 | 1 | 4 | 2 | 16 |
| *Haemophilus influenzae* Holt[d] | 16 | 16 | NT[f] | NT | NT | 64 | NT | NT | NT | NT | 32 | 32 | 128 |
| *Haemophilus influenzae* R252[3] | 16 | 16 | NT | NT | NT | 64 | NT | NT | NT | NT | 16 | 16 | 128 |

| | 14 | 15 | 16 | 17 | 18 | 19 | 20 | 21 | 22 | 23 | 24 | 25 |
|---|---|---|---|---|---|---|---|---|---|---|---|---|
| *Staphylococcus aureus* X1.1 | 0.5 | 0.5 | 0.5 | 0.5 | 1 | 1 | >128 | 8 | 0.25 | 0.5 | 0.5 | 0.5 |
| *Staphylococcus aureus* V41[b] | 1 | 1 | 0.5 | 1 | 1 | 1 | >128 | 16 | 0.5 | 1 | 1 | 1 |
| *Staphylococcus aureus* X400[c] | 2 | 1 | 1 | 1 | 1 | 1 | >128 | 16 | 0.5 | 1 | 0.5 | 1 |
| *Staphylococcus aureus* S13E | 1 | 0.5 | 0.5 | 0.5 | 1 | 1 | >128 | 8 | 0.5 | 0.5 | 0.5 | 0.5 |
| *Staphylococcus epidermidis* EPI1 | 0.5 | 0.5 | 0.5 | 0.5 | 1 | 1 | >128 | 8 | 0.5 | 0.5 | 0.5 | 1 |
| *Staphylococcus epidermidis* EPI2 | 2 | 1 | 1 | 1 | 2 | 1 | >128 | 16 | 1 | 1 | 1 | 2 |
| *Streptococcus pyogenes* C203 | 0.5 | 0.5 | 0.125 | 0.25 | 0.5 | 0.25 | 128 | 4 | 0.25 | 0.5 | 0.5 | 0.5 |
| *Streptococcus pneumoniae* Park I | 0.125 | 0.06 | 0.06 | 0.06 | 0.06 | 0.03 | 32 | 0.5 | 0.125 | 0.06 | 0.125 | 0.25 |
| Streptococcus Group D X66 | 2 | 2 | 0.5 | 1 | 1 | 1 | >128 | 8 | 0.5 | 1 | 1 | 1 |
| Streptococcus Group 9960 | 1 | 1 | 0.5 | 1 | 1 | 1 | >128 | 16 | 0.5 | 1 | 0.5 | 1 |
| *Haemophilus influenzae* Holt[d] | 8 | 64 | 4 | 16 | 32 | 8 | NT | NT | NT | NT | 8 | 32 |
| *Haemophilus influenzae* R252[e] | 8 | 32 | 2 | 8 | 32 | 8 | NT | NT | NT | NT | 8 | 16 |

[a]Compound numbers from Tables I and II
[b]Penicillin-resistant strain
[c]Methicillin-resistant-strain
[d]Ampicillin-sensitive strain
[e]Ampicillin-resistant strain
[f]NT = not tested

TABLE IV

Antibiotic Activity of 4"- and 3-Ester Derivatives

| Test Organism | Test Compound[a] | | | | | | | | | |
|---|---|---|---|---|---|---|---|---|---|---|
| | 1 | 2 | 3 | 4 | 5 | 6 | 7 | 9 | 10 | 14 |
| *Staphylococcus aureus* | 3.12 | 0.78 | 0.78 | 0.78 | 50 | 1.56 | 12.5 | 1.56 | 1.56 | 1.56 |
| Streptococcus sp. 80 | 0.78 | 0.39 | 0.78 | 1.56 | 1.56 | 0.39 | 0.78 | 1.56 | 1.56 | 1.56 |
| *Pasteurella multocida* 17E[b] | 12.5 | 6.25 | 12.5 | 12.5 | >50 | 50 | >50 | >50 | 25 | 12.5 |
| *Pasteurella multocida* 60A[c] | 25 | 12.5 | 12.5 | 25 | >50 | >50 | >50 | >50 | 50 | 25 |
| *Mycoplasma gallisepticum* | 0.39 | 0.097 | 0.097 | 0.195 | 1.56 | ≦0.048 | 0.78 | 0.78 | ≦0.05 | 0.39 |
| *Mycoplasma synoviae* | 0.78 | 0.39 | 0.78 | 0.39 | 12.5 | 0.39 | NT | 0.78 | 0.39 | 0.195 |
| *Mycoplasma hyorhinis* | 1.56 | 0.78 | 0.39 | 0.78 | 6.25 | 0.195 | 0.78 | 0.78 | 0.78 | 6.25 |

| | 15 | 17 | 18 | 19 | 20 | 21 | 22 | 23 | 24 | 25 |
|---|---|---|---|---|---|---|---|---|---|---|
| *Staphylococcus aureus* | 1.56 | 1.56 | 0.78 | 3.12 | 25 | 12.5 | 3.12 | 1.56 | 0.78 | 1.56 |
| Streptococcus sp. 80 | 1.56 | 0.78 | 0.39 | 0.195 | 50 | 6.25 | 1.56 | 1.56 | 0.39 | 1.56 |
| *Pasteurella multocida* 17E[b] | 50 | 25 | 12.5 | 6.25 | 50 | >50 | 25 | 50 | 6.25 | 25 |
| *Pasteurella multocida* 60A[c] | 50 | 50 | >50 | 12.5 | 50 | 50 | 25 | >50 | 12.5 | 50 |

TABLE IV-continued

| Test Organism | Antibiotic Activity of 4"- and 3-Ester Derivatives Test Compound[a] | | | | | | | | | |
|---|---|---|---|---|---|---|---|---|---|---|
| *Mycoplasma gallisepticum* | 0.39 | 0.097 | 0.39 | 0.195 | 6.25 | 0.78 | 0.195 | 0.39 | 0.097 | 0.195 |
| *Mycoplasma synoviae* | 0.39 | 0.195 | NT | 0.39 | 50 | 6.25 | 0.78 | 3.12 | 0.78 | 0.39 |
| *Mycoplasma hyorhinis* | 3.12 | 3.12 | 0.78 | 0.39 | 50 | 3.12 | 1.56 | 1.56 | 3.12 | 1.56 |

[a] Compound numbers from Tables I and II.
[b] Bovine isolate.
[c] Avian isolate.
[d] NT = not tested.

The ester derivatives of this invention have shown in vivo antimicrobial activity against experimental bacterial infections caused by gram-positive bacteria. When two doses of test compound were administered to mice with experimental infections, the activity observed was measured as an $ED_{50}$ value [effective dose in mg/kg to protect 50% of the test animals: see Warren Wick, et al., *J. Bacteriol.* 81, 233–235 (1961)]. $ED_{50}$ values observed for illustrative compounds are given in Table V.

TABLE V

| | $ED_{50}$ Values of 4"- and 3-Esters[a] | |
|---|---|---|
| | *Streptococcus pyogenes* C203 | |
| Test Compound[b] | Subcutaneous | Oral |
| 1 | NT[c] | 179 |
| 2 | NT | 117 |
| 4 | 12 | >150 |
| 5 | NT | >144 |
| 5 | >20 | >150 |
| 10 | 13 | >150 |
| 22 | >30 | 91 |
| 23 | >30 | >100 |
| 24 | 22 | 71 |
| 25 | >30 | 36 |

[a] mg/kg × 2; doses given 1 and 5 hours post-infection
[b] Compound numbers from Tables I and II
[c] NT = not tested This invention also relates to methods of controlling gram-positive and Mycoplasma infections. In carrying out the methods of this invention, an effective amount of a compound of formula 1 is administered parenterally or orally to an infected or susceptible warm-blooded animal. A susceptible animal is one which is threatened by the infection and is likely to develop it, if infected. The dose which is effective to control gram-positive or Mycoplasma infections will vary with the severity of the infection, the route of drug administration and the age, weight, and condition of the animal. The total dose required for protection parenterally will generally, however, be in the range of from about 1 to about 100 mg/kg and preferably will be in the range of from about 1 to about 50 mg/kg. The dose required for oral administration will generally be in the range of from about 1 to about 300 mg/kg and preferably will be in the range of from about 1 to about 100 mg/kg. Suitable dosage regimens can be constructed.

In another aspect, this invention relates to compositions useful for the control of gram-positive or Mycoplasma infections. These compositions comprise a compound of formula 1 together with a suitable pharmaceutical vehicle. Such compositions may be formulated for parenteral or oral administration by methods recognized in the pharmaceutical art. Effective compositions containing these compounds may be in either suspension or solution form. In the preparation of suitable formulations it will be recognized that, in general, the water solubility of the acid addition salts is greater than that of the free bases. Similarly, the bases are more soluble in dilute acids or in acidic conditions than in neutral or basic solutions.

In the solution form the compound is dissolved in a physiologically acceptable vehicle. Such vehicles comprise a suitable solvent, preservatives such as benzyl alcohol, if needed, and buffers. Useful solvents include, for example, water and aqueus alcohols, glycols, and carbonate esters such as diethyl carbonate. Such aqueous solutions contain, in general, no more than 50% of the organic solvent by volume.

Suspension compositions employ a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making suspensions in individual cases. For example, silicone antifoams, sorbitol, and sugars can be useful suspending agents.

In order to illustrate more fully the operation of this invention, the following examples are provided.

PREPARATION 1

Preparation of DMT

A. Shake-flask Fermentation of DMT

A lyophilized pellet of *Streptomyces fradiae* NRRL 12170 is dispersed in 1-2 ml of sterilized water. A portion of this solution (0.5 ml) is used to inoculate a vegetative medium (150 ml) having the following composition:

| Ingredient | Amount (%) |
|---|---|
| Corn steep liquor | 1.0 |
| Yeast extract | 0.5 |
| Soybean grits | 0.5 |
| CaCO$_3$ | 0.3 |
| Soybean oil (crude) | 0.45 |
| Deionized water | 97.25 |

Alternatively, a vegetative culture of *S. fradiae* NRRL 12170, preserved in 1-ml volumes in liquid nitrogen, is rapidly thawed and used to inoculate the vegetative medium. The inoculated vegetative medium is incubated in a 500-ml Erlenmeyer flask at 29° C. for about 48 hours on a closed-box shaker at 300 rpm.

This incubated vegetative medium (0.5 ml) is used to inoculate 7 ml of a production medium having the following composition:

| Ingredient | Amount (%) |
| --- | --- |
| Beet molasses | 2.0 |
| Corn meal | 1.5 |
| Fish meal | 0.9 |
| Corn gluten | 0.9 |
| NaCl | 0.1 |
| $(NH_4)_2HPO_4$ | 0.04 |
| $CaCO_3$ | 0.2 |
| Soybean oil (crude) | 3.0 |
| Deionized water | 91.36 |

The inoculated fermentation medium is incubated in a 50-ml bottle at 29° C. for about 6 days on a closed-box shaker at 300 rpm.

B. Tank Fermentation of DMT

In order to provide a larger volume of inoculum, 1200 ml of incubated vegetative medium, prepared in a manner similar to that described in section A, is used to inoculate 250 gallons of a second-stage vegetative growth medium having the following composition:

| Ingredient | Amount (%) |
| --- | --- |
| Corn steep liquor | 1.0 |
| Soybean oil meal | 0.5 |
| Yeast extract | 0.5 |
| $CaCO_3$ | 0.3 |
| Soybean oil (crude) | 0.5 |
| Lecithin (crude) | 0.015 |
| Water | 97.185 |

Adjust pH to 8.5 with 50% NaOH solution.

This second-stage vegetative medium is incubated in a 350-gallon tank for about 48 hours at 28° C., with adequate aeration and agitation.

Incubated second-stage medium (144 gallons) thus prepared is used to inoculate 1000 gallons of sterile production medium having the following composition:

| Ingredient | Amount (%) |
| --- | --- |
| Fish meal | 0.875 |
| Corn meal | 1.5 |
| Corn gluten | 0.875 |
| $CaCO_3$ | 0.2 |
| NaCl | 0.1 |
| $(NH_4)_2HPO_4$ | 0.04 |
| Beet molasses | 2.0 |
| Soybean oil (crude) | 3.0 |
| Lecithin | 0.09 |
| Water | 91.32 |

Adjust pH to 7.2 with 50% NaOH solution.

The inoculated production medium is allowed to ferment in a 1600-gallon tank for 8 to 9 days at a temperature of 28° C. The fermentation medium is aerated with sterile air to keep the dissolved oxygen level between about 30% and 50% and is stirred with conventional agitators at about 250 rpm.

C. Isolation of DMT

Harvested whole broth (3800 L), obtained as described in Section B, is filtered, using a filter aid. The mycelial cake is washed with water; this water wash is added to the filtrate.

The pH of the filtrate is adjusted to pH 9.2, using a 50% aqueous solution of sodium hydroxide (9.5 L). The filtrate is extracted with ethyl acetate (2000 L). Deionized water (450 L) and sodium phosphate monobasic (6.4 kg) are added to the ethyl acetate extract with thorough mixing. The pH of this mixture is adjusted from about pH 6.0 to pH 4.35, using a phosphoric acid solution (3300 ml; 2 parts water to one part phosphoric acid). The aqueous phase is separated. The pH of the enriched aqueous phase is adjusted to pH 6.5 using a 50% aqueous sodium hydroxide solution (700 ml).

The resulting solution is concentrated to a volume of about 225 L under vacuum. The pH of the concentrated solution is adjusted to pH 9.2 by the addition of 10% aqueous sodium hydroxide (16 L). The resulting basic solution is permitted to stand overnight. The crystals which form are separated by filtration, washed with deionized water (50 L), and dried to give about 8.6 kg of product. The product thus obtained can be recrystallized from acetone-water.

PREPARATION 2

2'-O-Acetyl-DMT

DMT (10 g, 13.5 mmol) was dissolved in acetone (260 ml) and treated with acetic anhydride (1.6 ml, 15.7 mmol) dropwise with stirring at room temperature. After stirring overnight (18 hours), the solvent was evaporated under reduced pressure. The residue thus obtained was dissolved in ethyl acetate (200 ml), and this solution was extracted with saturated $NaHCO_3$ solution (2×200 ml). The organic solution was dried ($Na_2SO_4$), filtered and evaporated. The residue was dissolved in a small volume of ethyl acetate, loaded on a silica gel column (Waters Prep 500) and eluted with ethyl acetate (4 liters). Fractions containing the desired product were identified by TLC, combined and evaporated to dryness, yielding 6.5 g (61%) of 2'-O-acetyl-DMT.

PREPARATION 3

2'-O-Propionyl-DMT

In a manner analogous to Preparation 2, DMT (6.0 g, 8.1 mmol) in acetone (120 ml) was treated with propionic anhydride (1.2 ml, 9.2 mmol). After workup and chromatography, 3.7 g (57%) of 2'-O-propionyl-DMT was isolated.

PREPARATION 4

Preparation of DMOT

A. Shake-flask Fermentation of DMOT

Following the procedures of Preparation 1, section A, but using a lyophilized pellet of *Streptomyces fradiae* NRRL 12171, DMOT is produced by shake-flask fermentation.

B. Tank Fermentation of DMOT

In order to provide a larger volume of inoculum, 60 ml of incubated vegetative medium, prepared in a manner similar to that described in section A, is used to inoculate 38 L of a second-stage vegetative growth medium having the same composition as that used for DMT in Preparation 1, Section B. This second-stage vegetative medium is incubated in a 68-liter tank for about 47 hours at 29° C.

Incubated second-stage medium (4 L) thus prepared is used to inoculate 40 liters of sterile production medium having the following composition:

| Ingredient | Amount (%) |
| --- | --- |
| Fish meal | 0.9188 |
| Corn meal | 1.575 |
| Corn gluten | 0.9188 |
| CaCO$_3$ | 0.210 |
| NaCl | 0.105 |
| (NH$_4$)$_2$HPO$_4$ | 0.042 |
| Beet molasses | 2.10 |
| Soybean oil (crude) | 3.15 |
| Lecithin | 0.0945 |
| Water | 90.8859 |

Adjust pH to 7.2 with 50% NaOH solution.

The inoculated production medium is allowed to ferment in a 68-liter tank for about 5 days at a temperature of 28° C. The fermentation medium is aerated with sterile air to keep the dissolved oxygen level between about 30% and 50% and is stirred with conventional agitators at about 300 rpm.

C. Isolation of DMOT

Fermentation broth, obtained as described in Section B, and having a pH of 7.2, is filtered using a filter aid. Ethyl acetate (400 ml) is added to the filtrate (1450 ml). The pH of the solution is adjusted to 9.1 by the addition of sodium hydroxide. The solution is stirred 10 minutes, and the ethyl acetate is separated (filtering through a filter aid to clear any emulsion which forms). The filtrate is again extracted with ethyl acetate (200 ml). Water (200 ml) is added to the combined ethyl acetate extracts; the pH of this solution is adjusted to 4.1 with phosphoric acid. After extraction, the aqueous phase is separated, and the organic phase is discarded. The aqueous phase is adjusted to pH 9.1 with sodium hydroxide and then concentrated to a volume of about 100 ml under vacuum. An amorphous precipitate forms. After permitting the precipitate to stand overnight, it is separated by filtration. The precipitated is dissolved in acetone (20 ml); water (75 ml) is added. The solution is concentrated under vacuum to remove acetone. The precipitate which forms is separated by filtration and washed with water to give about 500 mg of DMOT (1). An additional 260 mg is obtained in a similar manner from the filtrate.

PREPARATION 5

2'-O-Acetyl-DMOT

DMOT (5.0 g, 6.9 mmol), obtained as described in Preparation 4, was dissolved in acetone (150 ml) and treated with acetic anhydride (0.84 ml, 8.2 mmol) dropwise with stirring at room temperature. After stirring for 17 hours, solvent was evaporated under reduced pressure. The residue was dissolved in a small volume of ethyl acetate and chromatographed on silica gel (Waters Prep 500). Elution was carried out with ethyl acetate (4 liters). Fractions containing the desired product were combined and evaporated to dryness under reduced pressure to yield 4.2 g (80%) of 2'-O-acetyl-DMOT.

EXAMPLE 1

2'-O-Acetyl-23,4''-Di-O-Phenylacetyl-DMT

2'-O-Acetyl-DMT (2.75 g, 3.5 mmol) was dissolved in dichloromethane (75 ml) and pyridine (0.8 ml) and treated with a solution of phenylacetyl chloride (0.56 ml., 3.5 mmol) in dichloromethane (13 ml) dropwise with stirring at room temperature. After 1.5 hours, additional phenylacetyl chloride (0.56 ml) in dichloromethane (13 ml) was added. After another 1.5 hours, starting material had been consumed (TLC analysis). The solution was then evaporated to dryness under reduced pressure; the residue was dissolved in dichloromethane; and this solution was extracted with saturated NaHCO$_3$ solution. The organic layer was dried (Na$_2$SO$_4$), filtered and evaporated to dryness. The residue was dissolved in toluene and chromatographed on a silica gel column (Waters Prep 500). Elution was conducted with a linear gradient of 1:1 toluene-ethyl acetate (4 liters) and ethyl acetate (4 liters). Fractions containing the desired product were located by TLC, combined and evaporated to yield 0.8 g (24%) of 2'-O-acetyl-23,4''-di-O-phenylacetyl-DMT. Later fractions from this column gave 1.1 g (35%) of 2'-O-acetyl-23-O-phenylacetyl-DMT.

EXAMPLE 2

23,4''-Di-O-Phenylacetyl-DMT

2'-O-Acetyl-23,4''-di-O-phenylacetyl-DMT (0.36 g, 0.36 mmol) was dissolved in 80% aqueous methanol (30 ml) and refluxed for 4.5 hours. The solution was cooled to room temperature and evaporated to dryness under reduced pressure to yield 0.29 g (84%) of 23,4''-di-O-phenylacetyl-DMT.

EXAMPLE 3

2'-O-Acetyl-3,23,4''-Tri-O-Propionyl-DMT and

2'-O-Acetyl-23,4''-Di-O-Propionyl-DMT

2'-O-acetyl-DMT (2 g, 2.6 mmol) was dissolved in acetone (40 ml) and pyridine (8 ml) and treated with a solution of propionic anhydride (40 ml) in acetone (20 ml) dropwise with stirring at room temperature. After being stirred for 5 days, the mixture was evaporated under reduced pressure. The residual oil was dissolved in ethyl acetate, and this solution was extracted with saturated NaHCO$_3$ solution. The organic layer was dried (Na$_2$SO$_4$), filtered and evaporated. The residue was dissolved in a small volume of toluene, and this solution was chromatographed on silica gel (Waters Prep 500). The column was eluted with a linear gradient of toluene (4 liters) and ethyl acetate (4 liters). Fractions containing the desired product were located by TLC, combined and evaporated to yield 1.4 g (57%) of 2'-O-acetyl-3,23,4''-tri-O-propionyl-DMT and 0.67 g of 2'-O-acetyl-23,4''-di-O-propionyl-DMT.

EXAMPLE 4

3,23,4''-Tri-O-Propionyl-DMT

2'-O-Acetyl-3,23,4''-tri-O-propionyl-DMT (0.7 g, 0.74 mmol) was dissolved in 80% aqueous methanol (55 ml). The solution was refluxed for 5 hours, cooled, and then evaporated to remove the methanol under reduced pressure. The product was extracted into methylene chloride. The organic layer was separated, dried (Na$_2$SO$_4$), filtered and evaporated under reduced pressure to dryness to give 0.38 gm (56%) of 3,23,4''-tri-O-propionyl-DMT.

EXAMPLE 5

2',4'',23-Tri-O-Acetyl-DMT

DMT (10.0 g, 13.5 mmol) was dissolved in pyridine (150 ml) and treated with acetic anhydride (5.8 ml, 60.7 mmol) with stirring at room temperature. After the reaction was stirred overnight, the solvent was evaporated under reduced pressure. The residual oil was dissolved in dichloromethane, and this solution was washed with saturated NaHCO$_3$ solution. The organic layer was separated, dried (Na$_2$SO$_4$), filtered and evaporated under reduced pressure. The residual material was chromatographed on a silica-gel column (Waters Prep 500), eluting with a linear gradient of 3:1 toluene-ethyl acetate (4 liters) and ethyl acetate (4 liters). Fractions containing the desired product were identified by TLC, combined and evaporated under reduced pressure to yield 4.5 g of 2',4'',23-tri-O-acetyl-DMT.

EXAMPLE 6

23,4''-Di-O-Acetyl-DMT

2',4'',23-Tri-O-acetyl-DMT (1.65 g), prepared as described in Example 5, was dissolved in 80% aqueous methanol (70 ml), and the solution was refluxed for 4 hours. The solution was cooled and then concentrated to remove methanol under reduced pressure. The resulting aqueous mixture was partitioned between dichloromethane and saturated sodium bicarbonate solution. The organic layer was separated, dried over sodium sulfate and filtered; and the filtrate was evaporated under reduced pressure. The residue obtained was purified by flash chromatography on silica gel (E. Merck, grade 60), eluting stepwise with 3:1 toluene:acetonitrile (300 ml), 2:1 toluene:acetonitrile (200 ml) and 1:1 toluene:acetonitrile (400 ml). Fractions containing pure product were located by TLC, combined and evaporated to dryness to yield 0.31 g of 23,4''-di-O-acetyl-DMT.

EXAMPLE 7

Trichloroacetate Derivatives of DMT

2'-O-Acetyl-DMT (10 g, 12.8 mmol) was dissolved in dichloromethane (50 ml) and pyridine (50 ml). This solution was cooled in an ice bath and treated dropwise with a solution of trichloroacetic anhydride (4 ml) in dichloromethane (10 ml). After being stirred for 2.5 hr., the solution was diluted with toluene (100 ml) and evaporated to dryness under reduced pressure. The residue was dissolved in dichloromethane (100 ml). This solution was extracted with saturated sodium bicarbonate solution and then dried over sodium sulfate. The dried solution was filtered, and the filtrate was evaporated under reduced pressure. The residue was dissolved in a small volume of toluene and loaded on a silica-gel column wetted with toluene (Waters Prep 500). The column was eluted with a linear gradient of toluene (4 liters) and ethyl acetate (4 liters); fractions were collected and analyzed by TLC. Appropriate fractions were combined and evaporated under reduced pressure to yield, in order of elution: 0.78 g of 2'-O-acetyl-3,23,4''-tri-O-trichloroacetyl-DMT; 0.78 g of 2'-O-acetyl-23,4''-di-O-trichloroacetyl-DMT; 1.07 g of 2'-O-acetyl-3,23-di-O-trichloroacetyl-DMT and 5.88 g of 2'-O-acetyl-23-O-trichloroacetyl-DMT.

EXAMPLE 8

2'-O-Acetyl-4''-O-Propionyl-23-O-Trichloroacetyl-DMT

2'-O-Acetyl-23-O-trichloroacetyl-DMT (3.6 g, 3.9 mmol) was dissolved in acetone (50 ml) and pyridine (12 ml). To this solution was added a solution of propionic anhydride (6 ml) in acetone (10 ml). After being stirred at room temperature for 48 hours, the solution was diluted with toluene (100 ml) and evaporated under reduced pressure. The residue was dissolved in dichloromethane (75 ml), and this solution was extracted with saturated sodium bicarbonate solution and then dried over sodium sulfate. The dried solution was filtered, and the filtrate was evaporated under reduced pressure. The residue was dissolved in a small volume of toluene and loaded on a silica-gel cartridge wetted with toluene (Waters Prep 500). The cartridge was eluted with a linear gradient of toluene (4 liters) and ethyl acetate (4 liters). Fractions were analyzed by TLC. Appropriate fractions were combined and evaporated to dryness to yield 0.21 g of 2'-O-acetyl-4''-O-propionyl-23-O-trichloroacetyl-DMT, 1.5 g of recovered starting material and 0.97 g of a mixture of the two compounds.

EXAMPLE 9

4''-O-Propionyl-DMT

2'-O-Acetyl-4''-O-propionyl-23-O-trichloroacetyl-DMT (150 mg, 0.15 mmol) was dissolved in 80% aqueous methanol (15 ml), and this solution was refluxed for 8 hours. The solution was cooled and evaporated under reduced pressure to give 114 mg of 4''-O-propionyl-DMT.

EXAMPLE 10

2'-O-Acetyl-3,4''-Di-O-Propionyl-23-O-Trichloroacetyl-DMT

2'-O-Acetyl-23-O-trichloroacetyl-DMT (2.0 g, 2.2 mmol) was dissolved in pyridine (35 ml), and this solution was treated dropwise with propionic anhydride (6.8 ml). The reaction mixture was stirred at room temperature for 24 hours and then was diluted with toluene (50 ml) and evaporated to dryness under reduced pressure. The residue was dissolved in dichloromethane (35 ml). This solution was extracted with saturated sodium bicarbonate solution and then dried over sodium sulfate. The dried solution was filtered, and the filtrate was evaporated under reduced pressure. The residue was dissolved in a small volume of toluene and loaded on a silica gel cartridge wetted with toluene (Waters Prep 500). The cartridge was eluted with a linear gradient of toluene (4 liters) and ethyl acetate (4 liters). Fractions were analyzed by TLC, and appropriate fractions were combined and evaporated to dryness to yield 0.51 g of 2'-O-acetyl-3,4''-di-O-propionyl-23-O-trichloroacetyl-DMT.

EXAMPLE 11

3,4''-Di-O-Propionyl-DMT

2'-O-Acetyl-3,4''-di-O-propionyl-23-O-trichloroacetyl-DMT (450 mg) was dissolved in 80% aqueous methanol (45 ml) and refluxed for 4.5 hours. The solution was cooled and evaporated under reduced pressure. The residue obtained was dissolved in a small volume of dichloromethane and purified by flash chromatography; the crude product was loaded on a silica gel column (E. Merck grade 60) which was wetted with dichloromethane and eluted first with a linear gradient of dichloromethane (300 ml) and 5% methanol in dichloromethane (300 ml) and then with additional 5% methanol in dichloromethane (200 ml).

Fractions containing the desired product were located by TLC, combined and evaporated to dryness to yield 200 mg of 3,4''-di-O-propionyl-DMT.

EXAMPLE 12

23,4''-Di-O-Propionyl-DMT

2'-O-Acetyl-23,4''-di-O-propionyl-DMT (87 mg) was dissolved in 80% aqueous methanol (7 ml), and the solution was refluxed for 5 hours. The solution was cooled and evaporated to dryness under reduced pressure. The residue was dissolved in dichloromethane, dried over sodium sulfate and then filtered. The filtrate was evaporated to dryness to yield 42 mg of 23,4''-di-O-propionyl-DMT.

EXAMPLE 13

2'-O-Acetyl-4'',23-Di-O-Phenoxyacetyl-DMT and
2'-O-Acetyl-3,23-Di-O-Phenoxyacetyl-DMT 2'-O-Acetyl-DMT (2.75 g, 3.5 mmol) was dissolved in dichloromethane (75 ml) and pyridine (0.8 ml) and treated with a solution of phenoxyacetyl chloride (1.2 ml, 8.8 mmol) in dichloromethane (25 ml) dropwise with stirring at room temperature. After 1 hour, the reaction mixture was poured into saturated NaHCO₃ solution (200 ml). The organic layer was separated, dried (Na₂SO₄), filtered and evaporated under reduced pressure. The residual solid foam was loaded onto a flash-chromatography silica-gel column and eluted using 1:1 toluene-ethyl acetate. Based on TLC results, fractions were combined and evaporated to dryness to give 1.5 g of 2'-O-acetyl-23-O-phenoxyacetyl-DMT, 0.55 g of 2'-O-acetyl-4'',23-di-O-phenoxyacetyl-DMT, and 0.03 g of 2'-O-acetyl-3,23-di-O-phenoxyacetyl-DMT.

EXAMPLE 14

2'-O-Acetyl-4''-O-Phenylacetyl-DMOT

2'-O-Acetyl-DMOT (2.7 g, 3.5 mmol) was dissolved in dichloromethane (70 ml) and pyridine (0.8 ml) and treated with a solution of 0.56 ml (3.5 mmol) phenylacetyl chloride in dichloromethane (30 ml) dropwise with stirring at room temperature. After the reaction was stirred for 6 hours, solvent was evaporated. The residue was dissolved in dichloromethane and extracted with saturated NaHCO₃ solution. The organic layer was separated, dried (Na₂SO₄), filtered and evaporated. The residue was dissolved in ethyl acetate and chromatographed on silica gel (Waters Prep 500). The column was eluted with ethyl acetate (4 liters). Fractions containing the desired product were combined and evaporated to dryness to yield 1.2 g (38%) of 2'-O-acetyl-4''-O-phenylacetyl-DMOT.

EXAMPLE 15

2'-O-Acetyl-4''-O-Isovaleryl-DMOT

In a similar manner, 2'-O-acetyl-DMOT (1.2 g, 1.6 mmol) in pyridine (29 ml) was treated with isovaleryl chloride (0.7 ml, 3.8 mmol) with stirring at 0° C. After workup, the crude product was dissolved in toluene and chromatographed on silica gel by flash chromatography. The column was eluted with mixtures of toluene-:ethyl acetate (9:1 up to 1:2), yielding only 0.12 g of the product. Elution of the column with dichloromethane then yielded an additional 0.30 g of 2'-O-acetyl-4''-O-isovaleryl-DMOT.

EXAMPLE 16

4''-O-Isovaleryl-DMOT

2'-O-Acetyl-4''-O-isovaleryl-DMOT (0.4 g, 0.47 mmol) was dissolved in 80% aqueous methanol (30 ml) and refluxed for 4.5 hours. The solution was cooled to room temperature and evaporated to dryness under reduced pressure to yield 0.13 g (34%) of 4''-O-isovaleryl-DMOT.

EXAMPLE 17

4''-O-Phenylacetyl-DMOT

2'-O-Acetyl-4''-O-phenylacetyl-DMOT (0.2 g, 0.23 mmol) was dissolved in 80% aqueous methanol (18 ml) and refluxed for 5 hours. The solution was cooled to room temperature and evaporated to dryness under reduced pressure to yield 0.16 g (86%) 4''-O-phenylacetyl-DMOT.

EXAMPLE 18

2'-O-Acetyl-4''-O-Propionyl-DMOT and
2'-O-Acetyl-3,4''-Di-O-Propionyl-DMOT 2'-O-Acetyl-DMOT (1.0 g; 1.3 mmol) was dissolved in pyridine (30 ml) and treated with 0.6 ml (4.6 mmol) propionic anhydride dropwise with stirring at room temperature. After 20 hours, an additional 3.0 ml (23 mmol) propionic anhydride was added and the reaction was stirred for an additional 26 hours at room temperature. The mixture was diluted with toluene (30 ml), and volatiles were evaporated under reduced pressure. The residual oil was dissolved in dichloromethane (50 ml) and extracted with saturated NaHCO₃ solution; the organic layer was separated, dried (Na₂SO₄), filtered and evaporated. The residue was loaded on a silica gel column (Waters Prep 500) and eluted with a linear gradient of toluene (4 liters) and ethyl acetate (4 liters). 2'-O-acetyl-3,4''-di-O-propionyl-DMOt (305 mg) was eluted first, followed by 2'-O-acetyl-4''-O-propionyl-DMOT (286 mg).

EXAMPLE 19

4''-O-Propionyl-DMOT and
3,4''-Di-O-propionyl-DMOT

2'-O-Acetyl-4''-O-propionyl-DMOT and 2'-O-acetyl-3,4''-di-O-propionyl-DMOT, prepared as described in Example 18, were each dissolved in methanol and refluxed for above five hours. Each solution was cooled to room temperature and evaporated to dryness under reduced pressure to give 4''-O-propionyl-DMOT and 3,4''-di-O-propionyl-DMOT, respectively.

EXAMPLE 20

Injectable Formulations (A) A formula 1 base is added to propylene glycol. Water and benzyl alcohol are added so that the solution contains 50% (by volume) propylene glycol, 4% (by volume) benzyl alcohol, and 200 mg/ml of a formula 1 base.

(B) A solution is prepared as described in Section A except that the solution contains 50 mg/ml of a formula 1 base.

(C) A solution is prepared as described in Section A except that the solution contains 350 mg/ml of a formula 1 base.

(D) A solution is prepared as described in Section A except that the solution contains 500 mg/ml of a formula 1 tartrate.

(E) A suspension is prepared by adding a finely ground formula 1 compound to carboxymethyl cellulose with thorough mixing so that the suspension contains 200 mg of the formula 1 base per ml of suspension.

I claim:

1. A compound of the formula

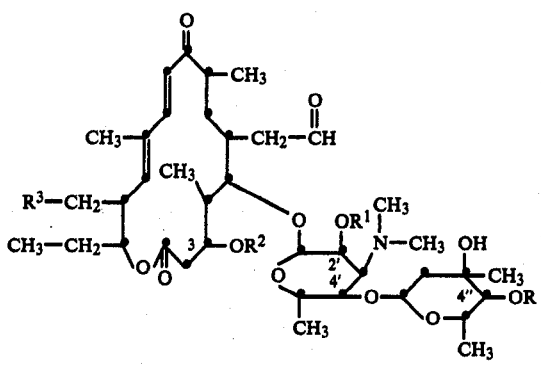

wherein

R is hydrogen, $C_1$-$C_5$-alkanoyl, $C_1$-$C_5$-alkanoyl having from one to three halo substituents, benzoyl, phenylacetyl, or phenoxyacetyl or benzoyl, phenylacetyl or phenoxyacetyl having on the phenyl ring from one to five halo or methyl or from one to two methoxyl, nitro, or hydroxyl groups;

$R^1$ is hydrogen, $C_1$-$C_5$-alkanoyl, $C_1$-$C_5$-alkanoyl having from one to three halo substituents, benzoyl, phenylacetyl, or phenylpropionyl or benzoyl, phenylacetyl, or phenylpropionyl having on the phenyl ring from one to five halo or methyl or from one to two methoxyl, nitro, or hydroxyl groups;

$R^2$ is hydrogen, $C_1$-$C_5$-alkanoyl, $C_1$-$C_6$-alkanoyl having from one to three halo substituents, benzoyl, phenylacetyl, phenylpropionyl, phenoxyacetyl, or phenylthioacetyl or benzoyl, phenylacetyl, phenylpropionyl, phenoxyacetyl or phenylthioacetyl having on the phenyl ring from one to five halo or methyl or from one to two methoxy, nitro, or hydroxyl groups;

$R^3$ is hydrogen or $R^4O$—; and $R^4$ is hydrogen or an acyl group selected from:

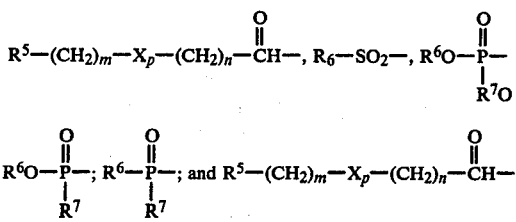

substituted by one or two halo, ethyl, methoxy, amino, N-protected amino, methylamino, dimethylamino, nitro, acetoxy, acetamido, azido, carbomethoxy, carboxamido, cyano, or hydroxyl groups, provided that, when the substituent is other than halo or alkyl, there can be no more than one substituent on any connecting —$CH_2$— group;

p is 0 or 1; m and n are integers from 0 to 4;

$R^5$ is hydrogen, halo, $C_1$-$C_4$-alkyl, $C_3$-$C_8$-cycloalkyl, phenyl, $C_5$-$C_8$-cycloalkenyl, naphthyl, indenyl, tetralinyl, decalinyl, adamantyl,1-ethyl-1,4-dihydro-4-oxo[1,3]dioxolo[4,5-g]cinnolin-3-yl(cinnoxacinyl), a monocyclic heterocyclic ring system comprising 3 to 8 atoms or a bicyclic heterocyclic ring system comprising 6 to 11 atoms, provided that at least 1 atom of the ring system is carbon and at least 1 atom of the ring system is a heteroatom selected from O, N, and S;

X is O, S, —NH—, —N($CH_3$)—, —C≡C—, —CH=CH—, —C($CH_3$)=CH—, —CH=C($CH_3$)— or —C($CH_3$)=C($CH_3$)—; and $R^6$ and $R^7$ are $C_1$-$C_5$-alkyl or optionally substituted phenyl or benzyl;

and further provided that one of R or $R^2$ must be other than hydrogen and that, when $R^1$ is hydrogen, $R^3$ is hydrogen or —OH and $R^2$ is acetyl, R cannot be hydrogen, acetyl, n-butyryl or isovaleryl and, when R and $R^1$ are hydrogen and $R^3$ is hydrogen or OH, $R^2$ cannot be propionyl; and the acid addition salts thereof.

2. A compound of claim 1 wherein $R^3$ is $R^4O$— and the acid addition salt thereof.

3. A compound of claim 2 wherein $R^4$ is hydrogen and the acid addition salts thereof.

4. A compound of claim 2 wherein $R^4$ is other than hydrogen and the acid addition salts thereof.

5. A compound of claim 4 wherein $R^4$ is

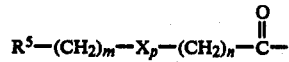

and the addition salts thereof.

6. A compound of claim 5 wherein $R^5$ is hydrogen or $C_1$-$C_4$-alkyl and the acid addition salts thereof.

7. A compound of claim 5 wherein p is 0 and the acid addition salts thereof.

8. A compound of claim 5 wherein $R^5$ is phenyl or phenyl having from one to five halo or methyl or from one to two methoxy, nitro, or hydroxyl substituents and the acid addition salts thereof.

9. A compound of claim 5 wherein X is oxygen or —NH— and n is 0 and the acid addition salts thereof.

10. A compound of claim 5 wherein X is oxygen or sulfur and n is 1 and the acid addition salts thereof.

11. A compound of claim 4 wherein $R^4$ is $R^6SO_2$ and the acid addition salts thereof.

12. A compound of claim 11 wherein $R^6$ is phenyl or phenyl having from one to five halo or methyl or from one to two methoxyl, nitro, or hydroxyl substituents and the acid addition salts thereof.

13. A compound of claim 2 wherein R is $C_1$-$C_5$-alkanoyl or $C_1$-$C_5$-alkanoyl having from one to three halo substituents and the acid addition salts thereof.

14. A compound of claim 2 wherein $R^2$ is $C_1$-$C_5$-alkanoyl or $C_1$-$C_5$-alkanoyl having from one to three halo substituents and the acid addition salts thereof.

15. A compound of claim 14 wherein R is $C_1$-$C_5$-alkanoyl or $C_1$-$C_5$-alkanoyl having from one to three halo substituents and the acid addition salts thereof.

16. A compound of claim 13 wherein R is acetyl and its acid addition salts.

17. The compound of claim 16 wherein $R^2$ is hydrogen, $R^1$ is hydrogen or acetyl, and $R^4$ is acetyl and its acid addition salts.

18. A compound of claim 13 wherein R is propionyl and its acid addition salts.

19. The compound of claim 18 wherein $R^1$ is hydrogen or acetyl, $R^2$ is hydrogen and $R^4$ is propionyl and its acid addition salts.

20. The compound of claim 18 wherein $R^1$ is hydrogen or acetyl and $R^2$ and $R^4$ are propionyl and its acid addition salts.

21. The compound of claim 18 wherein $R^1$ is acetyl, $R^2$ is hydrogen and $R^4$ is trichloroacetyl and its acid addition salts.

22. The compound of claim 18 wherein $R^1$, $R^2$ and $R^4$ are hydrogen and its acid addition salts.

23. The compound of claim 18 wherein $R^1$ is acetyl, $R^2$ is propionyl, and $R^4$ is trichloroacetyl and its acid addition salts.

24. The compound of claim 18 wherein $R^1$ and $R^4$ are hydrogen and $R^2$ is propionyl and its acid addition salts.

25. A compound of claim 2 wherein R is phenylacetyl and the acid addition salts thereof.

26. The compound of claim 25 wherein $R^1$ is hydrogen or acetyl, $R^2$ is hydrogen, and $R^4$ is phenylacetyl and its acid addition salts.

27. A compound of claim 2 wherein R is phenoxyacetyl and the acid addition salts thereof.

28. The compound of claim 27 wherein $R^1$ is hydrogen or acetyl, $R^2$ is hydrogen and $R^4$ is phenoxyacetyl and its acid addition salts.

29. A compound of claim 2 wherein R is trichloroacetyl and its acid addition salts.

30. The compound of claim 29 wherein $R^1$ is acetyl, $R^2$ is hydrogen and $R^4$ is trichloroacetyl and its acid addition salts.

31. The compound of claim 29 wherein $R^1$ is acetyl and $R^2$ and $R^4$ are trichloroacetyl and its acid addition salts.

32. A compound of claim 2 wherein R is hydrogen and the acid addition salts thereof.

33. A compound of claim 32 wherein $R^2$ is $C_1$–$C_5$-alkanoyl or $C_1$–$C_5$-alkanoyl having from one to three halo substituents and the acid addition salts thereof.

34. A compound of claim 33 wherein $R^2$ is trichloroacetyl and the acid addition salts thereof.

35. The compound of claim 34 wherein $R^1$ is acetyl and $R^4$ is trichloroacetyl and its acid addition salts.

36. A compound of claim 2 wherein $R^2$ is benzoyl, phenylacetyl, phenylpropionyl, phenoxyacetyl or phenylthioacetyl having on the phenyl ring from one to five halo or methyl or from one to two methoxyl, nitro, or hydroxyl groups and the acid addition salts thereof.

37. A compound of claim 36 wherein $R^2$ is phenoxyacetyl and the acid addition salts thereof.

38. The compound of claim 37 wherein R is hydrogen, $R^1$ is hydrogen or acetyl and $R^4$ is phenoxyacetyl and its acid addition salts.

39. A compound of claim 1 wherein $R^3$ is hydrogen and its acid addition salts.

40. A compound of claim 39 wherein R is $C_1$–$C_5$-alkanoyl or $C_1$–$C_5$-alkanoyl having from one to three halo substituents and the acid addition salts thereof.

41. A compound of claim 40 wherein R is isovaleryl and its acid addition salts.

42. The compound of claim 41 wherein $R^1$ is hydrogen or acetyl and $R^2$ is hydrogen and its acid addition salts.

43. A compound of claim 39 wherein R is phenylacetyl and its acid addition salts.

44. The compound of claim 43 wherein $R^1$ is hydrogen or acetyl and $R^2$ is hydrogen and its acid addition salts.

45. A compound of claim 40 wherein R is propionyl and the acid addition salts thereof.

46. The compound of claim 45 wherein $R^1$ is hydrogen or acetyl and $R^2$ is hydrogen and its acid addition salts.

47. The compound of claim 45 wherein $R^1$ is hydrogen or acetyl and $R^2$ is propionyl and its acid addition salts.

48. A compound of claim 39 wherein $R^2$ is $C_1$–$C_5$-alkanoyl or $C_1$–$C_5$-alkanoyl having from one to three halo substituents and the acid addition salts thereof.

49. A compound of claim 39 wherein $R^2$ is benzoyl, phenylacetyl, phenylpropionyl, phenoxyacetyl or phenylthioacetyl having on the phenyl ring from one to five halo or methyl or from one to two methoxyl, nitro, or hydroxyl groups and the acid addition salts thereof.

50. A method for controlling susceptible gram-positive infections which comprises administering to an infected or susceptible warm-blooded animal an effective amount of a composition comprising a compound of claim 1, 2, 3, 4, or 39 or a pharmaceutically acceptable acid addition salt thereof and a suitable pharmaceutical vehicle.

51. A composition for the control of susceptible gram-positive infections comprising an amount of a compound of claim 1, 2, 3, 4, or 39 or a pharmaceutically acceptable acid addition salt thereof which is effective against such infections and a suitable pharmaceutical vehicle.

52. A method for controlling susceptible Mycoplasma infections which comprises administering to an infected or susceptible warm-blooded animal an effective amount of a compound of claim 1 or a pharmaceutically-acceptable acid addition salt thereof and a suitable pharmaceutical vehicle.

53. A composition for the control of Mycoplasma infections comprising an amount of a compound of claim 1 or a pharmaceutically-acceptable acid addition salt thereof which is effective against such infections together with a suitable pharmaceutical vehicle.

* * * * *